US011291356B2

(12) United States Patent
Wake (10) Patent No.: US 11,291,356 B2
(45) Date of Patent: Apr. 5, 2022

(54) INSERTION APPARATUS AND OPERATION METHOD FOR INSERTION APPARATUS

(71) Applicant: OLYMPUS CORPORATION, Tokyo (JP)

(72) Inventor: Fuminori Wake, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 247 days.

(21) Appl. No.: 16/573,205

(22) Filed: Sep. 17, 2019

(65) Prior Publication Data
US 2020/0022569 A1    Jan. 23, 2020

Related U.S. Application Data

(63) Continuation of application No. PCT/JP2018/006720, filed on Feb. 23, 2018.

(30) Foreign Application Priority Data

Mar. 27, 2017  (JP) .............................. JP2017-061777

(51) Int. Cl.
*A61B 1/015* (2006.01)
*A61B 1/00* (2006.01)
(Continued)

(52) U.S. Cl.
CPC .......... *A61B 1/015* (2013.01); *A61B 1/00006* (2013.01); *A61B 1/018* (2013.01);
(Continued)

(58) Field of Classification Search
CPC ..... A61B 1/015; A61B 1/00006; A61B 1/018; A61B 1/12; A61B 1/126–128;
(Continued)

(56) References Cited

U.S. PATENT DOCUMENTS 5,191,878 A * 3/1993 Iida ..................... A61B 1/00068
600/157
2001/0025135 A1* 9/2001 Naito ................... A61B 1/0014
600/156

(Continued)

FOREIGN PATENT DOCUMENTS

| JP | 2006-181108 A | 7/2006 |
|----|---------------|--------|
| JP | 2015-198821 A | 11/2015 |
| WO | WO 2015/019695 A1 | 2/2015 |

OTHER PUBLICATIONS

International Search Report dated Apr. 10, 2018 issued in PCT/JP2018/006720.

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

An insertion apparatus includes an endoscope, a first air feeding apparatus, a first air suction apparatus, a second air feeding apparatus, a second air suction apparatus, a pressure detector, an operation detector and a controller, and the controller performs first control on the second air feeding apparatus and the second air suction apparatus so that the amount of gas per predetermined time period fed from the second air feeding apparatus becomes equal to the amount of gas suctioned by the second air suction apparatus, and when the operation detector detects the operation and the pressure detector detects that the pressure in a subject changes from a first pressure to a second pressure, the controller maintains the first control to perform air feeding/air suction into/from the subject at the second pressure.

14 Claims, 7 Drawing Sheets

(51) Int. Cl.
    *A61B 1/018*   (2006.01)
    *A61B 18/14*   (2006.01)
    *A61B 18/00*   (2006.01)
(52) U.S. Cl.
    CPC .................. *A61B 18/1482* (2013.01); *A61B 2018/00595* (2013.01); *A61B 2218/008* (2013.01)
(58) Field of Classification Search
    CPC ...... A61B 18/1482; A61B 2018/00595; A61B 17/320016; A61B 17/3421; A61B 17/3423; A61B 2017/3437; A61B 2017/3445
    USPC .................. 600/156–158, 104, 153, 169
    See application file for complete search history.

(56) References Cited

U.S. PATENT DOCUMENTS

| | | | | |
|---|---|---|---|---|
| 2005/0234298 | A1* | 10/2005 | Kucklick | A61B 17/3423 600/156 |
| 2013/0303852 | A1* | 11/2013 | Hiraga | A61B 1/00068 600/118 |
| 2014/0371667 | A1* | 12/2014 | Kasuya | A61B 1/00135 604/26 |
| 2016/0106934 | A1 | 4/2016 | Hiraga et al. | |

\* cited by examiner

INSERTION APPARATUS AND OPERATION METHOD FOR INSERTION APPARATUS

CROSS REFERENCE TO RELATED APPLICATION

This application is a continuation application of PCT/JP2018/006720 filed on Feb. 23, 2018 and claims benefit of Japanese Application No. 2017-061777 filed in Japan on Mar. 27, 2017, the entire contents of which are incorporated herein by this reference.

BACKGROUND OF THE INVENTION

1. Field of the Invention

The present invention relates to an insertion apparatus equipped with an endoscope including an insertion portion to be inserted into a subject and an operation method for the insertion apparatus.

2. Description of the Related Art

Among insertion apparatuses equipped with an endoscope used in the medical field, a procedure is well known in which an insertion portion of the endoscope is inserted into a living body which is a subject, and a tissue to be treated in a biological tissue of the living body is observed under endoscopic observation, a cauterization apparatus inserted into a treatment instrument insertion tube through a treatment instrument insertion port provided at an operation portion of the endoscope is caused to project from an opening provided at the insertion portion, energy is given to the tissue to be treated from the projecting cauterization apparatus and the tissue to be treated is thereby resected or excised from the biological tissue.

For example, an ESD (endoscopic submucosal dissection) procedure in an endoscopic procedure for removing a lesion such as a cancer tissue in a living body under endoscopic observation is well known.

More specifically, for example, the ESD procedure is known as a treatment in which the insertion portion of the endoscope is inserted into the living body and a cancer tissue existing in the living body is brought into an observation view of the endoscope, a cauterization apparatus inserted into a treatment instrument insertion tube of the endoscope, for example, a high frequency knife is caused to project forward from a distal end of the insertion portion, then the insertion portion is moved forward or backward to remove the cancer tissue made to float in advance by injection of a dedicated liquid using the high frequency knife.

Here, during a procedure such as the ESD procedure in which a biological tissue is dissected and blood from bleeding is caused to coagulate, for example, the mucus and fat in the living body evaporate accompanying dissection and coagulation performed by applying a high frequency current from the high frequency knife to the cancer tissue, mucous membranes and fat become misty as a fluid containing solid particle components, or more specifically, as a gas containing components derived from the biological tissue.

As a result, especially in a long-lasting procedure such as an ESD procedure, a situation may occur in which a narrow space is easily filled with mist and the observation view of the endoscope is obstructed.

Therefore, in order to secure the observation view during the ESD procedure, it is preferable to use a technique that suctions a gas containing components derived from the biological tissue from an air suction port using an air suction tube. Note that a configuration in which the air suction tube also serves as a treatment instrument insertion tube is also well known.

Japanese Patent Application Laid-Open Publication No. 2015-198821 discloses a configuration in which a pressure of a living body is measured using a pressure sensor, and a gas is fed when the living body has a negative pressure compared to a first pressure and the gas is suctioned when the living body has a positive pressure.

SUMMARY OF THE INVENTION

An insertion apparatus according to an aspect of the present invention includes an endoscope including an insertion portion to be inserted into a subject of a living body, a first air feeding apparatus configured to feed gas into the subject based on operation from an outside, a first air suction apparatus configured to send gas from an inside of the subject to an outside of the subject based on operation from the outside, a second air feeding apparatus configured to continuously feed gas into the subject independently of the operation from the outside, a second air suction apparatus configured to continuously send to an outside of the subject, gas containing particles obstructing a view of the endoscope generated when a cauterization apparatus inserted into the subject jointly with the insertion portion gives energy to the living body from the inside of the subject independently of the operation from the outside, a pressure detector configured to detect a pressure in the subject, an operation detector configured to detect that operation on the first air feeding apparatus or the first air suction apparatus is performed and a controller configured to control an amount of gas fed into the subject on the second air feeding apparatus and control an amount of gas suctioned to the outside of the subject on the second air suction apparatus, in which the controller performs first control on the second air feeding apparatus and the second air suction apparatus so that the amount of gas fed from the second air feeding apparatus per predetermined time period is equal to the amount of gas suctioned by the second air suction apparatus, and when the operation detector detects the operation and the pressure detector detects that the pressure in the subject is changed from a first pressure to a second pressure, the controller maintains the first control so as to feed the gas into and suction the gas from the subject, the pressure of which becomes the second pressure.

An insertion apparatus according to another aspect of the present invention includes an endoscope including an insertion portion to be inserted into a subject, a first air feeding apparatus configured to feed gas into the subject based on operation from an outside, a first air suction apparatus configured to send gas from the inside of the subject to the outside of the subject based on operation from the outside, a second air feeding apparatus configured to continuously feed gas into the subject independently of the operation, a second air suction apparatus configured to continuously send gas from the inside of the subject to the outside of the subject independently of the operation, a pressure detector configured to detect a pressure variation value per predetermined time period in the subject or a time period during which a pressure in the subject changes, an operation detector configured to detect that operation on the first air feeding apparatus or the first air suction apparatus is performed and a controller configured to control an amount of gas fed into the subject on the second air feeding apparatus and control an amount of gas suctioned to the outside of the subject on the second air suction apparatus, in which the controller performs first control on the second air feeding apparatus and the second air suction apparatus so that the amount of gas fed from the second air feeding apparatus per predetermined time period is equal to the amount of gas suctioned by the second air suction apparatus, and when the operation detector detects the operation and the pressure detector detects that the pressure in the subject is changed from a first pressure to a second pressure, the controller maintains the first control so as to feed the gas into and suction the gas from the subject, the pressure of which becomes the second pressure.

Furthermore, an operation method for an insertion apparatus according to a further aspect of the present invention includes inserting an insertion portion of an endoscope into a subject of a living body, inserting a cauterization apparatus jointly with the insertion portion into the subject, detecting a pressure in the subject by a pressure detector, and continuously feeding gas into the subject by a second air feeding apparatus independently of the operation from an outside and continuously sending to the outside of the subject gas in the subject containing particles obstructing a view of the endoscope generated when the cauterization apparatus gives energy to the living body by the second air suction apparatus independently of the operation from the outside, in which the controller performs first control on the second air feeding apparatus and the second air suction apparatus so that the amount of gas fed from the second air feeding apparatus per predetermined time period is equal to the amount of gas suctioned by the second air suction apparatus, and when the operation detector detects the external operation on the first air feeding apparatus or the first air suction apparatus and the pressure detector detects that the pressure in the subject is changed from a first pressure to a second pressure, the controller maintains the first control so that the gas is fed into and the gas is suctioned from the subject, the pressure of which becomes the second pressure.

DETAILED DESCRIPTION OF THE PREFERRED EMBODIMENT(S)

Hereinafter, embodiments of the present invention will be described with reference to the accompanying drawings. Note that the drawings are schematic ones and a relationship between thickness and width of each member, thickness ratio among respective members are different from the actual ones, and it goes without saying that dimensional relationships and ratios differ among respective drawings.

Figure 1:
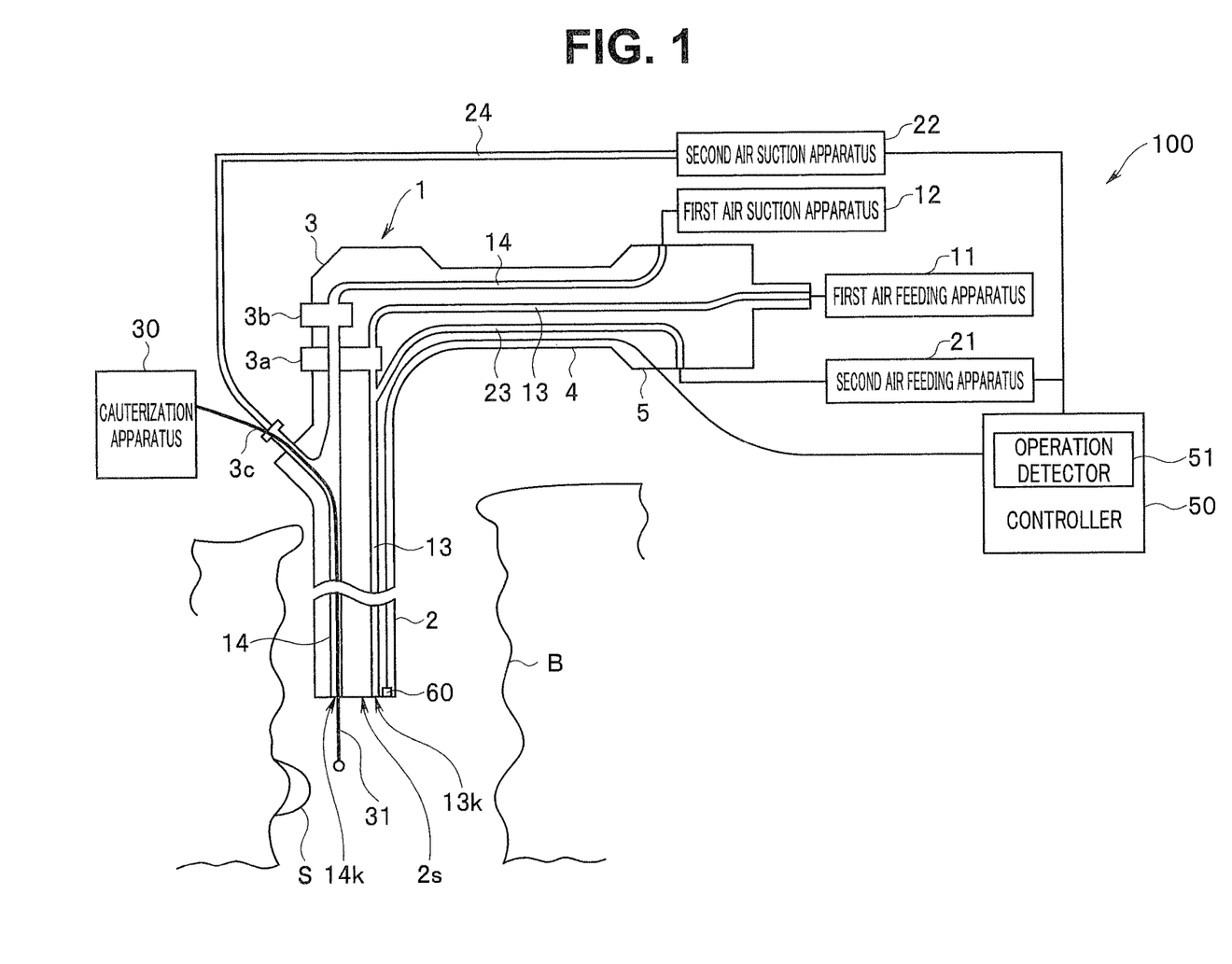
FIG. 1 is a diagram schematically illustrating a configuration of an insertion apparatus according to the present embodiment.
Figure 2:
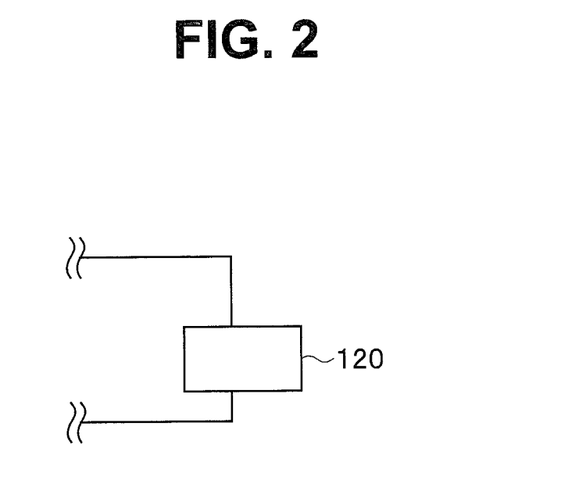
FIG. 2 is a diagram illustrating a modification in which a second air feeding apparatus and a second air suction apparatus in FIG. 1 are integrally formed.
Figure 3:
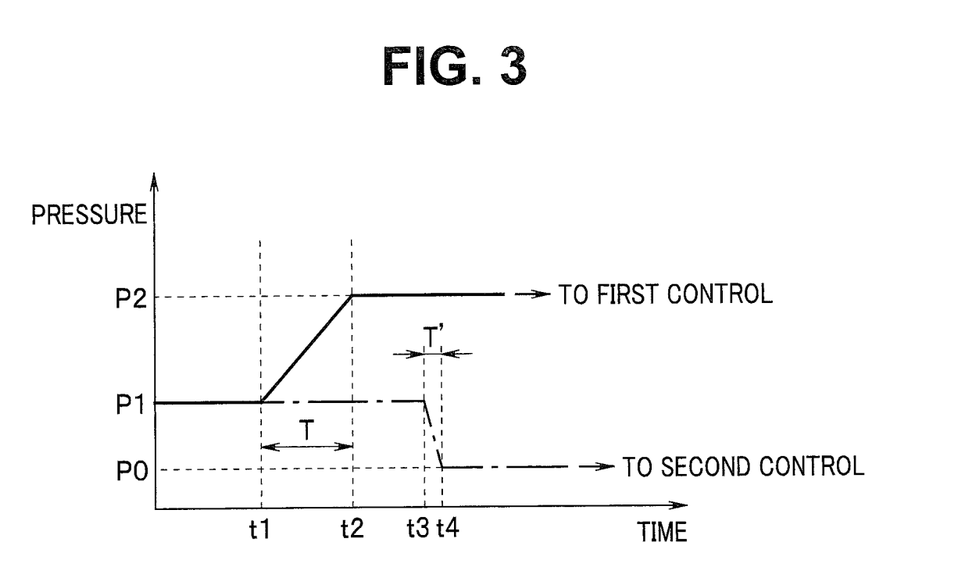
FIG. 3 is a diagram illustrating an example of pressure variation per predetermined time period in a subject.

FIG. 1 is a diagram schematically illustrating a configuration of an insertion apparatus according to the present embodiment, FIG. 2 is a diagram illustrating a modification in which a second air feeding apparatus and a second air suction apparatus in FIG. 1 are integrally formed and FIG. 3 is a diagram illustrating an example of pressure variation per predetermined time period in a subject.

As shown in FIG. 1, an insertion apparatus 100 is provided with an endoscope 1. Main parts of the endoscope 1 are constructed of an insertion portion 2 inserted into a subject B which is a living body, an operation portion 3 connected to a proximal end of the insertion portion 2, a universal cord 4 extending from the operation portion 3, and a connector 5 provided at an extending end of the universal cord 4 and freely attachable/detachable to/from an external apparatus.

A first air feeding tube 13, a distal end of which is open at a distal end of the insertion portion 2 as an air feeding port 13$k$ and a proximal end of which is open to the connector 5 is provided in the endoscope 1.

Note that the first air feeding tube 13 is connected to a first air feeding apparatus 11 in the connector 5. An example of the first air feeding apparatus 11 is a pump. Furthermore, the air feeding port 13$k$ may not necessarily be open at the distal end of the insertion portion 2 but may be at a midway position of the insertion portion 2.

The first air feeding apparatus 11 is configured to feed a predetermined amount of gas into the subject B when an operator switches an air feeding switch 3$a$ provided at the operation portion 3 for switching whether or not to send gas to the first air feeding tube 13.

A first air suction tube 14, a distal end of which is open at the distal end of insertion portion 2 as an air suction port 14$k$, a proximal end of which is open to the connector 5 and part of which is open to a forceps port 3$c$ at the operation portion 3 is provided in the endoscope 1.

Note that the first air suction tube 14 is connected to a first air suction apparatus 12 in the connector 5. An example of the first air suction apparatus 12 is a pump. Furthermore, the air suction port 14$k$ may not necessarily be open at the distal end of the insertion portion 2, but may be at a midway position of the insertion portion 2.

Note that a high frequency treatment instrument 31 of a cauterization apparatus 30 inserted into the subject B jointly with the insertion portion 2 through the forceps port 3$c$ is freely attachable/detachable to/from the first air suction tube 14.

The distal end side of the high frequency treatment instrument 31 is made to project into the subject B via the air suction port 14k and used for treatment on a lesion S, which is a biological tissue in the subject B.

The first air suction apparatus 12 is configured to send a predetermined amount of gas from the inside of the subject B to the outside of the subject when the operator switches an air suction switch 3b for switching whether or not to suction the gas by the first air suction tube 14 provided in the first air suction tube 14 of the operation portion 3.

A second air feeding tube 23, a distal end of which is connected closer to the air feeding port 13k side than the air feeding switch 3a in the first air feeding tube 13 and a proximal end of which is open to the connector 5 is provided in the endoscope 1.

In other words, the second air feeding tube 23 branches from the first air feeding tube 13 and also converges with the first air feeding tube 13 at least in the insertion portion 2. Note that it goes without saying that the second air feeding tube 23 may also be provided separately from the first air feeding tube 13.

Furthermore, the second air feeding tube 23 is connected to a second air feeding apparatus 21 in the connector 5. Note that an example of the second air feeding apparatus 21 is a pump.

The second air feeding apparatus 21 is connected to a controller 50 and is configured to continuously feed gas into the subject B via the second air feeding tube 23 under operation control by the controller 50 independently of operation by the operator.

The insertion apparatus 100 includes a second air suction tube 24, a distal end of which is connected to the forceps port 3c and a proximal end of which is connected to a second air suction apparatus 22.

In other words, the second air suction tube 24 branches from the first air suction tube 14 and also converges with the first air suction tube 14 at least in the insertion portion 2. Note that it goes without saying that the second air suction tube 24 may also be provided separately from the first air suction tube 14.

Furthermore, an example of the second air suction apparatus 22 is a pump. Note that as shown in FIG. 2, the second air feeding apparatus 21 and the second air suction apparatus 22 may also be constructed of a pump 120 in which an air feeding mechanism and an air suction mechanism for filtering gas sent from the inside of the subject and feeding the gas into the subject again are integrated.

The second air suction apparatus 22 is connected to the controller 50 and is configured to continuously send gas from the inside of the subject B to the outside of the subject B via the second air suction tube 24 under the operation control by the controller 50 independently of operation by the operator.

The second air suction apparatus 22 is configured to suction gas containing particles obstructing a view of the endoscope 1 generated when the high frequency treatment instrument 31 of the cauterization apparatus 30 gives energy to the living body.

A pressure detector 60 configured to detect a pressure in the subject is provided at the distal end of the insertion portion 2. Note that an example of the pressure detector 60 is a pressure sensor. The pressure detector 60 is connected to the controller 50.

Note that the pressure detector 60 may also be provided at the air feeding switch 3a, the air suction switch 3b, or the forceps port 3c, on an outer surface of the distal end portion of the insertion portion 2 or at a pressure detection instrument, etc., configured to pass through the tube in the insertion portion 2 and protrude from the distal end of the insertion portion 2.

The pressure detector 60 is configured to detect a degree of variation of pressure in the subject B such as a value of variation in pressure per predetermined time period in the subject B, a time period during which the pressure in the subject B changes, a time period during which a pressure variation continues in the subject B based on the operation of the first air feeding apparatus 11 or the first air suction apparatus 12.

An operation detector 51 configured to detect operation of the first air feeding apparatus 11 or the first air suction apparatus 12 by the operator is provided in the controller 50.

As shown in FIG. 3, when a variation time period T during which a pressure detected by the pressure detector 60 changes from a pressure P1 to a pressure P2 continues for a predetermined time period or more such as t1 to t2, the operation detector 51 detects operation of the first air feeding apparatus 11 or the first air suction apparatus 12 by the operator.

When a variation time period T' during which a pressure detected by the pressure detector 60 changes from the pressure P1 to a pressure P0 is less than a predetermined time period such as t3 to t4, the operation detector 51 assumes that the pressure variation in the subject B is not attributable to operation of the first air feeding apparatus 11 or the first air suction apparatus 12 by the operator but to leakage of gas caused by burps (eructation) or the like from the inside of the examinee's body, and does not detect the operation of the first air feeding apparatus 11 or the first air suction apparatus 12.

Note that the operation detector 51 may also detect the operation of the first air feeding apparatus 11 or the first air suction apparatus 12 by the operator by detecting switch operation of the air feeding switch 3a or switch operation of the air suction switch 3b.

The controller 50 is configured to control an amount of gas fed into the subject B by the second air feeding apparatus 21 and also control an amount of gas sent from the inside of the subject B to the outside of the subject B by the second air suction apparatus 22.

More specifically, the controller 50 exercises first control on the second air feeding apparatus 21 and the second air suction apparatus 22 so that the amount of gas per predetermined time period fed from the second air feeding apparatus 21 becomes equal to the amount of gas suctioned by the second air suction apparatus 22.

Even when the pressure in the subject B somewhat changes from the first pressure P1, this prevents control on air feeding or air suction not intended by the operator to immediately restore the pressure in the subject B at the first pressure P1, and so the pressure in the subject B is less likely to change frequently.

Figure 5:
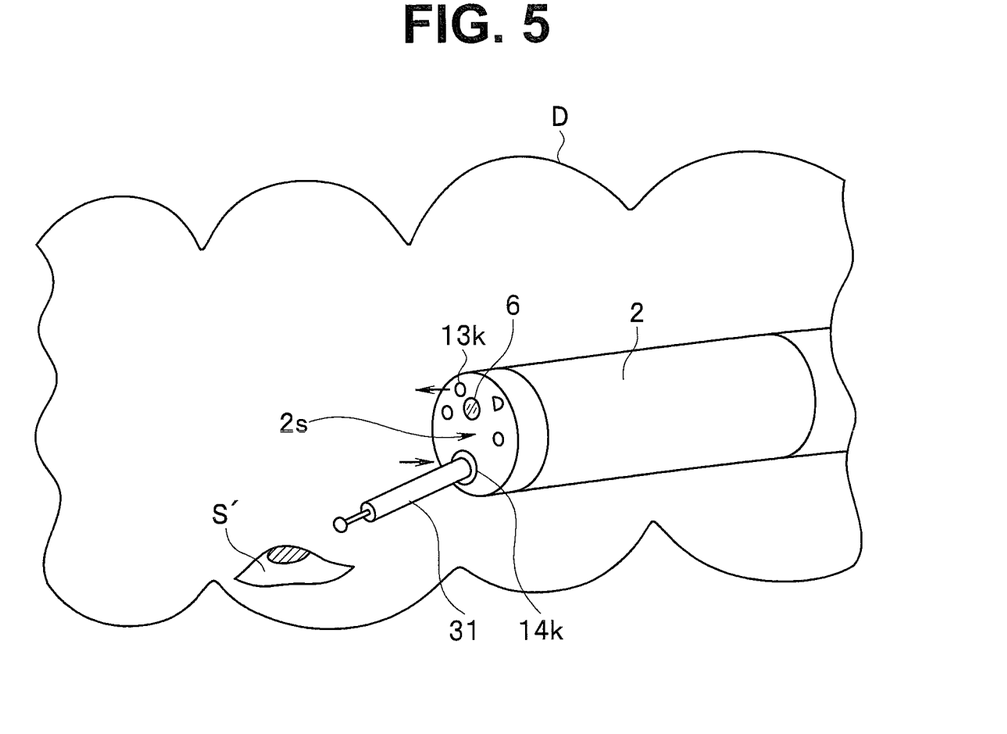
FIG. 5 is a diagram illustrating a situation in which an insertion portion of the endoscope in FIG. 1 is inserted into a digestive tract as an example of the subject to treat a lesion in the digestive tract using a high frequency treatment instrument of a cauterization apparatus.
Figure 6:
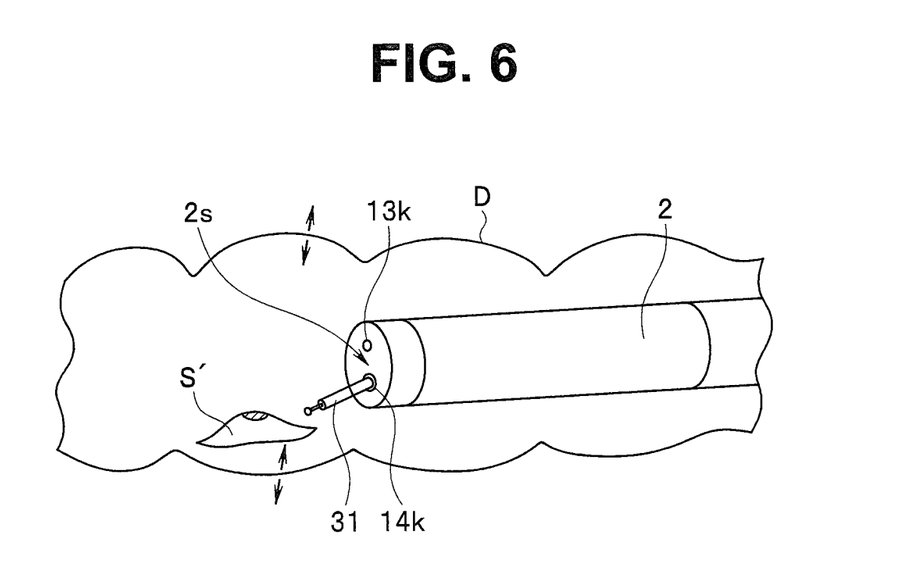
FIG. 6 is a diagram illustrating a situation in which the digestive tract in FIG. 5 vibrates due to frequent expansion and contraction.

Here, FIG. 5 is a diagram illustrating a situation in which the insertion portion of the endoscope in FIG. 1 is inserted into a digestive tract as an example of the subject to treat a lesion in the digestive tract using the high frequency treatment instrument of the cauterization apparatus and FIG. 6 is a diagram illustrating a situation in which the digestive tract in FIG. 5 vibrates due to frequent expansion and contraction.

Note that the reason why the first control is performed so that the amount of gas fed from the second air feeding apparatus 21 becomes equal to the amount of gas suctioned by the second air suction apparatus 22 is that when pressure adjustment not intended by the operator trying to cause the pressure in the digestive tract D to return to the first pressure P1 is frequently performed, the digestive tract D frequently expands and contracts due to a minute pressure variation caused by the pressure adjustment and an inner wall of the digestive tract D or a lesion S' vibrates as shown in FIG. 6, and so observability and treatment performance may be lowered.

Therefore, control needs to be exercised not on the pressure in the digestive tract D but such that the amount of gas fed becomes equal to the amount of gas suctioned in order for the digestive tract D not to frequently expand and contract but to be settled down (remain substantially stationary).

The controller 50 maintains the first control as shown in FIG. 3 when the operation detector 51 detects operation by the operator on the first air feeding apparatus 11 or the first air suction apparatus 12 and the pressure detector 60 detects that the pressure in the subject B changes from, for example, the first pressure P1 to the second pressure P2.

This prevents control on air feeding or air suction not intended by the operator to immediately restore the pressure in the subject B to the first pressure P1 from the second pressure P2 after the pressure variation following the completion of operation detection, making the pressure in the subject B less likely to change frequently.

Note that although a case is taken as an example in FIG. 3 where the second pressure P2 is higher than the first pressure P1, regardless of this case, the same applies to a case where the second pressure P2 is lower than the first pressure P1.

Furthermore, regardless of the detection by the operation detector 51, when the pressure detector 60 detects a pressure variation due to, for example, leakage of gas caused by burps (eructation) from the inside of the examinee's body as described above, the controller 50 performs second control so that the amount of gas fed from the second air feeding apparatus 21 is different from the amount of gas suctioned by the second air suction apparatus 22 so as to restore the first pressure P1 before the variation as shown in FIG. 3.

Note that although a case is taken as an example in FIG. 3 where the pressure P0 after the variation is lower than the first pressure P1, regardless of this case, the same applies to a case where the pressure P0 is higher than the first pressure P1.

In other words, the controller 50 performs gas circulation control on the subject B. Note that "circulation" means that gas circulates between the inside and outside of the subject.

Note that the rest of the configuration of the insertion apparatus 100 is the same as the configurations of the prior arts, and so description is omitted.

Figure 4:
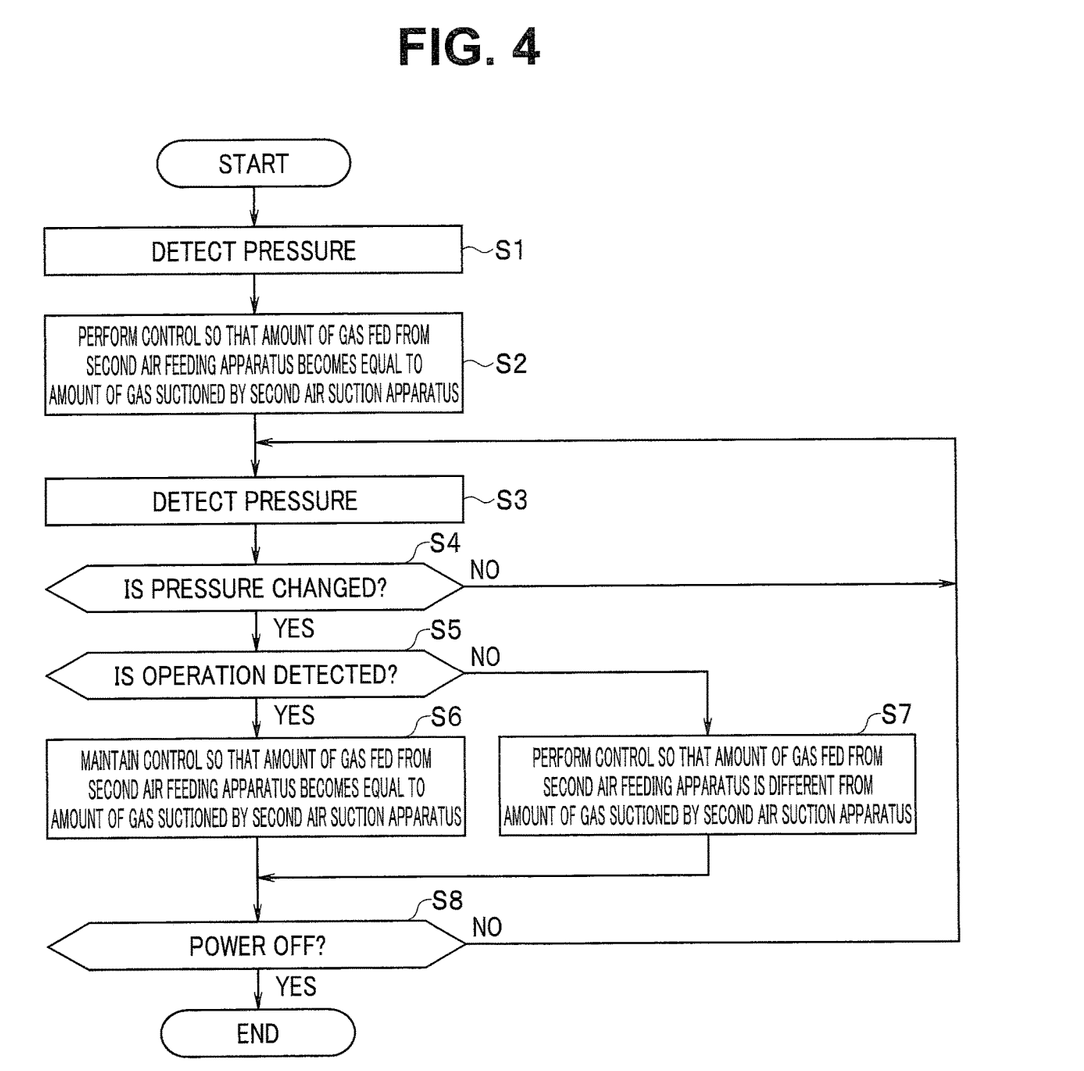
FIG. 4 is a flowchart illustrating circulation control according to a pressure variation in a subject by the controller in FIG. 1.

Next, operation of the present embodiment, or more specifically an operation method for the insertion apparatus 100 will be described using FIG. 4. FIG. 4 is a flowchart illustrating the circulation control by the controller in FIG. 1 according to a pressure variation in the subject.

After the insertion portion 2 is inserted into the subject B, the controller 50 first detects the pressure in the subject B via the pressure detector 60 in step S1.

Next, in step S2, the controller 50 performs the first control on the second air feeding apparatus 21 and the second air suction apparatus 22 so that the amount of gas per predetermined time period fed from the second air feeding apparatus 21 becomes equal to the amount of gas suctioned per predetermined time period by the second air suction apparatus 22.

More specifically, the controller 50 performs control to continuously feed the gas in the subject through the second air feeding apparatus 21 via the second air feeding tube 23 independently of the operation of the endoscope 1 by the operator and also control to continuously send the gas in the subject B to the outside of the subject B through the second air suction apparatus 22 via the second air suction tube 24 independently of the operation by the operator.

In this way, the pressure in the subject. B mostly becomes the first pressure P1 and the first pressure P1 is maintained.

Next, in step S3, the controller 50 detects the pressure in the subject B through the pressure detector 60 during the first control.

After that, in step S4, the controller 50 determines whether or not there is a pressure variation in the subject B. The controller 50 repeats the pressure detection in step S3 when there is no pressure variation or proceeds to step S5 when there is a pressure variation, and determines whether or not the operation detector 51 detects the operation of the air feeding switch 3*a* or the air suction switch 3*b*.

On the other hand, when no operation is detected, the controller 50 branches to step S7 and performs second control on the second air feeding apparatus 21 and the second air suction apparatus 22.

More specifically, regardless of the detection by the operation detector 51, when the pressure detector 60 detects a pressure variation, for example, when a pressure variation in the subject B is detected from burps (eructation) or the like of the examinee, the controller 50 performs control, as the second control, so that the amount of gas fed from the second air feeding apparatus 21 is different from the amount of gas suctioned by the second air suction apparatus 22.

By so doing, the pressure in the subject B mostly returns to the first pressure P1 before the pressure variation. Then, the controller 50 proceeds to step S8.

On the other hand, when the operation is detected, the controller 50 proceeds to step S6 and maintains the first control on the second air feeding apparatus 21 and the second air suction apparatus 22.

More specifically, when the operation detector 51 detects operation of the first air feeding apparatus 11 by the operator, a predetermined gas is fed into the subject B via the first air feeding tube 13 or operation of the first air suction apparatus 12 by the operator is detected, a predetermined amount of gas is sent from the inside of the subject B to the outside of the subject B via the first air suction tube 14, and the pressure detector 60 thereby detects a pressure variation in the subject B, the controller 50 maintains, as the first control, control so that the amount of gas fed from the second air feeding apparatus 21 becomes equal to the amount of gas suctioned by the second air suction apparatus 22.

By so doing, the pressure in the subject B transitions without significantly changing from the state after the pressure variation (mostly second pressure P2). The controller 50 then proceeds to step S8.

Finally, it is determined, in step S8, whether or not power to the endoscope 1 is turned off. On the other hand, as long as no power off is detected, the controller 50 returns to step S3 and repeatedly performs steps S3 to S8. On the other hand, when the power off is detected, the controller 50 ends the circulation control.

Thus, it has been shown in the present embodiment that when the operation detector 51 detects operation of the air feeding switch 3*a* or the air suction switch 3*b* and a pressure variation in the subject B is detected, the controller 50 maintains the first control so that the amount of gas fed from the second air feeding apparatus 21 and the amount of gas suctioned from the second air suction apparatus 22 are kept constant.

As shown above, even when the operator intentionally feeds gas into or suctions gas from the subject B, the pressure in the subject B after the air feeding or air suction does not significantly change, and so it is possible to drastically decrease the possibility that the interior of the subject or lesion S may cause vibration or unexpected operation due to a pressure variation and keep the interior of the subject and the lesion S settled down, that is, almost stationary, and thereby continue to remove components obstructing the observation view of the endoscope 1 generated in the subject B (components derived from the lesion S and surrounding tissues) without impairing the observability and treatment performance.

Note that the points described so far are especially effective when the subject is a digestive tract such as the stomach or the large intestine including a narrow space, that is, space with a small volume.

This is because the narrower the space, the more quickly the space is filled with mist (gas containing components derived from the lesion S and surrounding tissues) generated in a cauterization treatment using the cauterization apparatus 30 unless appropriate air suction is performed, making it no longer possible to secure the observation view.

This is also because unless appropriate balance between air suction and air feeding is achieved for a narrower space, the subject may drastically expand or contract, an appropriate positional relationship between the endoscope 1 or the high frequency treatment instrument 31 and the lesion S is likely to be lost against the intention of the operator and the interior of the subject or the lesion S is likely to cause vibration or an unexpected operation due to a slight pressure variation.

Therefore, the present embodiment exhibits effects especially in a treatment using a flexible scope executed by inserting the insertion portion of the endoscope 1 into the digestive tract rather than in a surgical treatment using, for example, a laparoscope executed by feeding gas into the subject and causing the subject to expand.

As described so far, it is possible to provide the insertion apparatus 100 and the operation method for the insertion apparatus 100 provided with a configuration in which when a treatment is performed by giving energy to the lesion S and when the operator intentionally changes the pressure in the subject B, it is possible to suppress a drastic pressure variation from the interior state of the subject while removing the gas containing components obstructing the observation view of the endoscope generated in the subject B.

Figure 7:
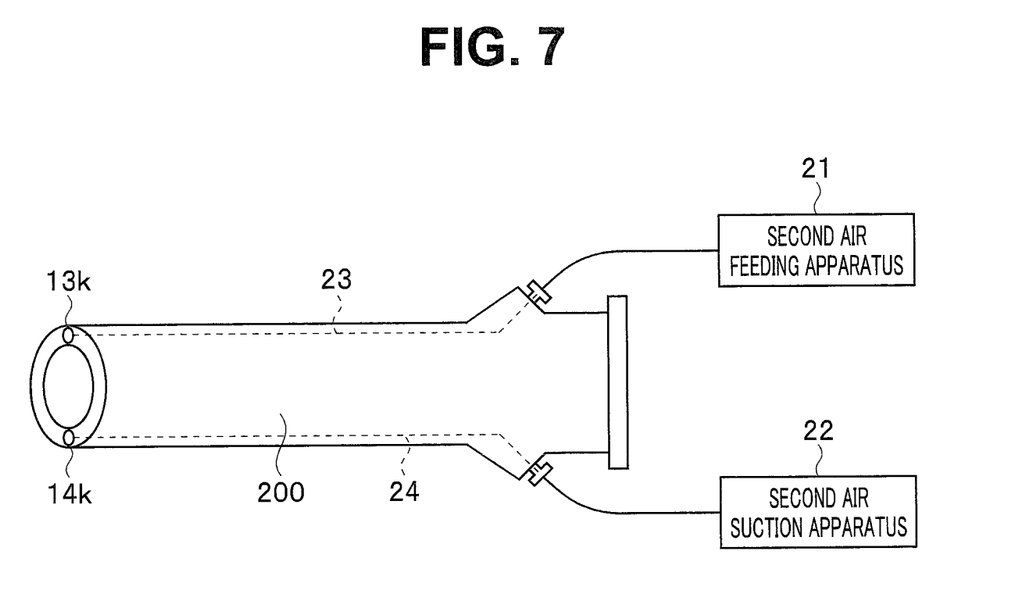
FIG. 7 is a diagram illustrating an overtube inserted into the subject with the insertion portion of the endoscope in FIG. 1 internally mounted therein, together with the second air feeding apparatus and the second air suction apparatus.

Hereinafter, modifications will be described using FIGS. 7 to 9. FIG. 7 illustrates an overtube inserted when the insertion portion of the endoscope in FIG. 1 is internally mounted, together with the second air feeding apparatus and the second air suction apparatus, FIG. 8 is a diagram illustrating the overtube in FIG. 7 inserted into the digestive tract with the insertion portion in FIG. 1 internally mounted therein and FIG. 9 is a front view of a distal end of the overtube in FIG. 8 as viewed from a point IX in FIG. 8.

Figure 8:
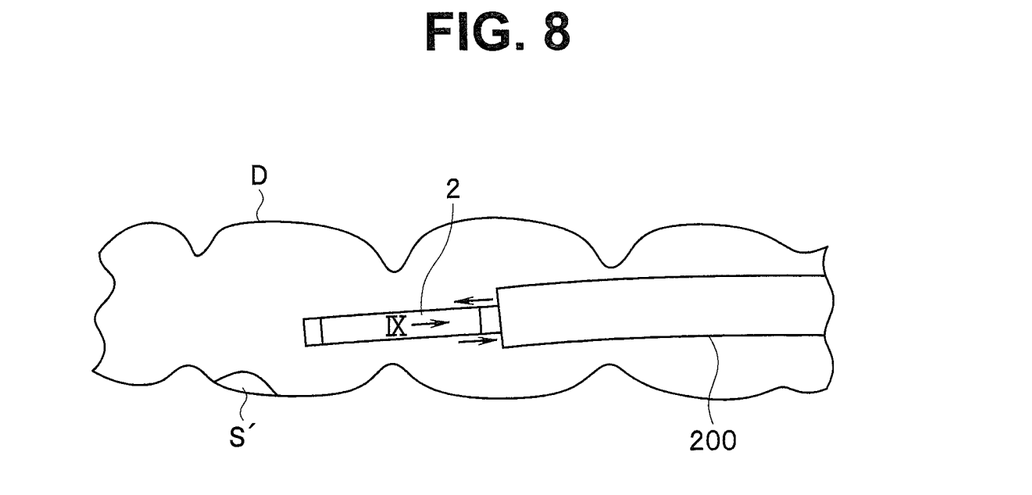
FIG. 8 is a diagram illustrating the overtube in FIG. 7 inserted into the digestive tract with the insertion portion in FIG. 1 internally mounted therein.
Figure 9:
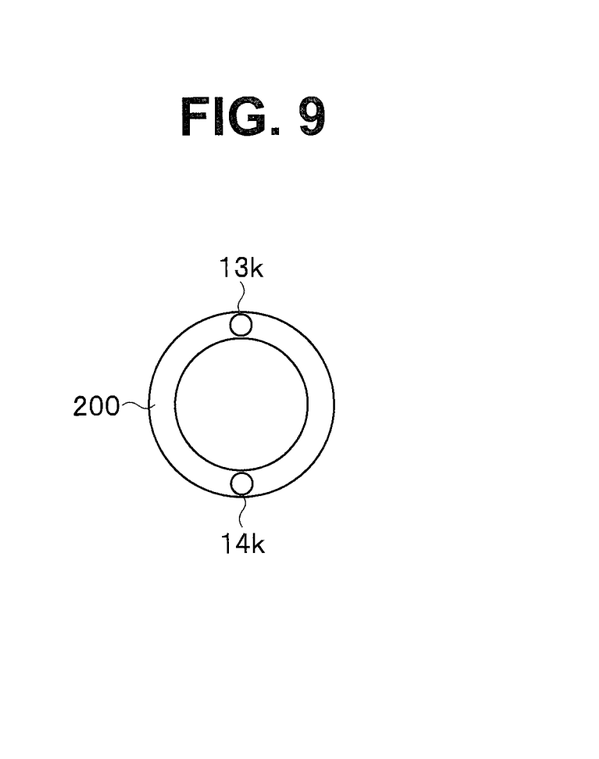
FIG. 9 is a front view of a distal end of the overtube in FIG. 8 as viewed from a point IX in FIG. 8.

As shown in FIGS. 7 to 9, the second air feeding tube 23 and the second air suction tube 24 configured to perform feeding and suction of gas in the digestive tract D under the circulation control by the controller 50 may be provided in an overtube 200 in which the insertion portion 2 of the endoscope 1 is internally mounted.

In this case, the air feeding port 13k and the air suction port 14k are opened at a distal end of the overtube 200.

Effects similar to the effects of the aforementioned present embodiment can be achieved by such a configuration as well.

Figure 10:
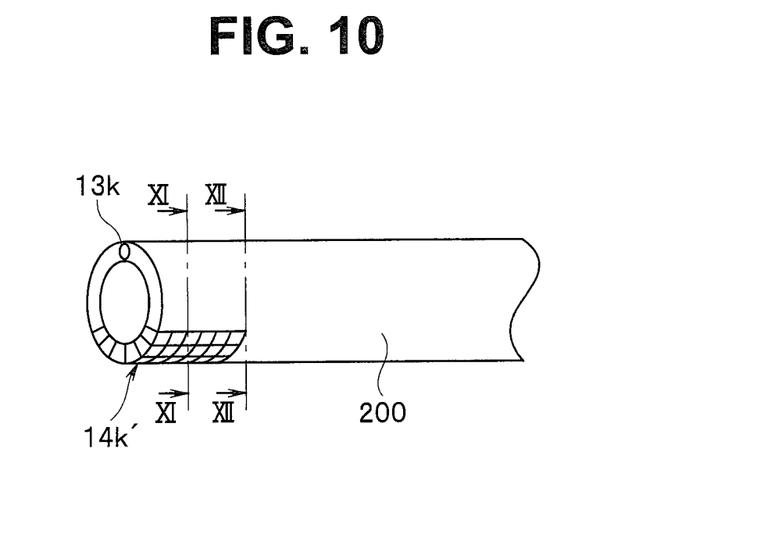
FIG. 10 is a diagram illustrating a modification in which a mesh-shaped air suction port is provided in the overtube in FIG. 7.

Furthermore, other modifications will be described below using FIGS. 10 to 12. FIG. 10 is a diagram illustrating a modification in which a mesh-shaped air suction port is provided in the overtube in FIG. 7, FIG. 11 is a cross-sectional view of the overtube along a line XI-XI in FIG. 10 and FIG. 12 is a cross-sectional view of the overtube along a line XII-XII in FIG. 10.

Figure 11:
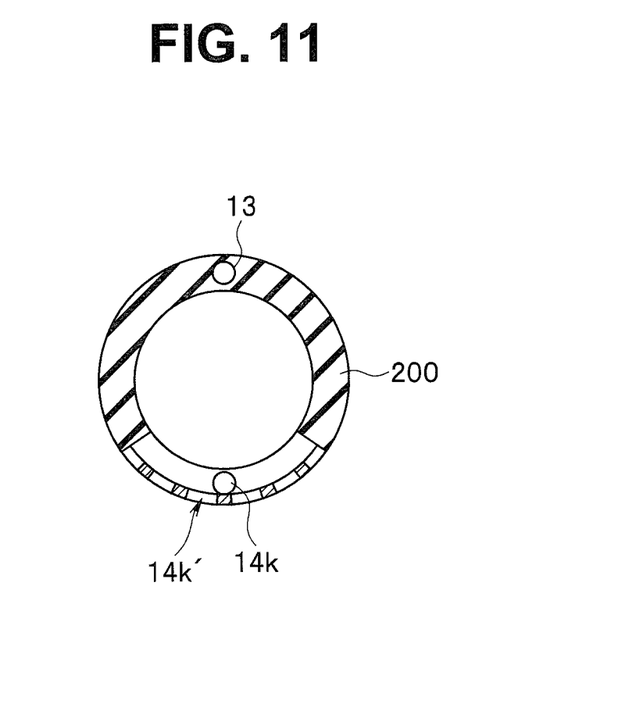
FIG. 11 is a cross-sectional view of the overtube along a line XI-XI in FIG. 10.
Figure 12:
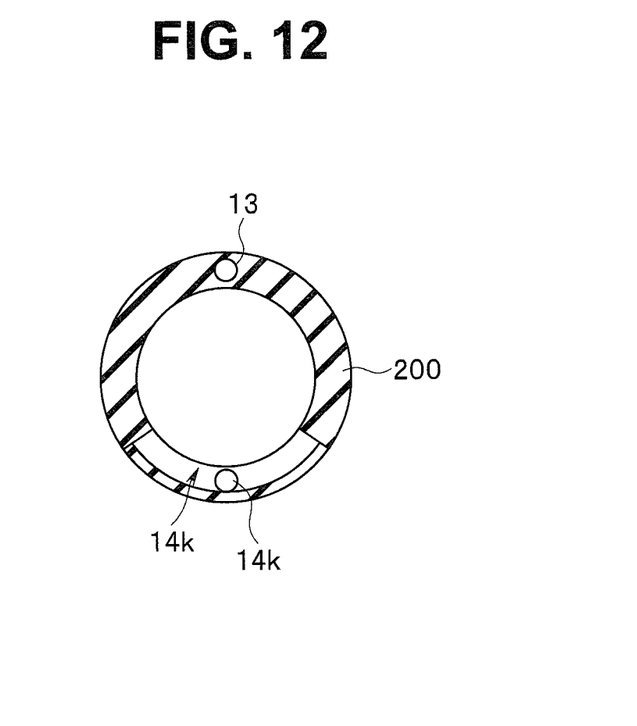
FIG. 12 is a cross-sectional view of the overtube along a line in FIG. 10.

As shown in FIGS. 10 to 12, an air suction port 14k' of the overtube 200 may be formed into a mesh shape with a greater diameter than the air suction port 14k shown in FIG. 7.

According to such a configuration, it is possible to prevent the air suction port 14k' from being closed with a mucous membrane or the like of the digestive tract D during suctioning of the interior of the subject B via the air suction port 14k'.

Effects similar to the effects of the aforementioned present embodiment can be achieved by such a configuration as well.

Although a case has been described in the aforementioned present embodiment where the pressure detector 60 is provided in the distal end of the insertion portion 2, regardless of such a case, it goes without saying that the pressure detector 60 may be provided at a treatment instrument or the like inserted into the subject B jointly with the aforementioned overtube 200, the high frequency treatment instrument 31 or other endoscope 1 or further inserted into the subject B via a tube.

In order to further prevent the operator from unintentionally move the lesion S or the like in front of the view of the endoscope 1, the shape of the air feeding port 13k may be devised such that gas fed from the second air feeding apparatus 21 is fed not in a longitudinal direction of the endoscope 1 but in a direction deviating from the longitudinal direction of the endoscope 1 (e.g., upward from the view).

What is claimed is:

1. An insertion apparatus comprising:
   an endoscope including an insertion portion to be inserted into a subject of a living body;
   a first air feeding pump configured to feed gas into the subject based on a first user input operation;
   a first air suction pump configured to suction gas from an inside of the subject to an outside of the subject based on a second user input operation;
   a second air feeding pump configured to continuously feed gas into the subject independently of the first user input operation;
   a second air suction pump configured to continuously suction gas from the inside of the subject to the outside of the subject independently of the second user input operation, the gas being generated when a cauterization apparatus inserted into the subject jointly with the insertion portion applies a high frequency current to the living body, the gas containing particles obstructing a view of the endoscope;
   a pressure sensor configured to detect a pressure in the subject;
   a controller configured to:
      control an amount of gas fed into the subject by the second air feeding pump;
      control an amount of gas suctioned to the outside of the subject by the second air suction pump,
      perform a first control of the second air feeding pump and the second air suction pump to maintain the pressure in the subject at a first pressure by controlling the amount of gas fed from the second air feeding pump per predetermined time period to be equal to the amount of gas suctioned by the second air suction pump, detect operation of the first air feeding pump or the first air suction pump, and when the operation of the first air feeding pump or the first air suction pump is detected and the pressure detector detects that the pressure in the subject is changed from the first pressure to a second pressure which is different from the first pressure, and the second pressure continues for a predetermined time period or more, continue the first control to maintain the second pressure in the subject.

2. The insertion apparatus according to claim 1, wherein when the pressure detector detects a pressure variation, the controller performs, independently of the detection of the operation of the first air feeding pump or the first air suction pump, a second control in which the amount of gas fed from the second air feeding pump is different from the amount of gas suctioned by the second air suction pump so as to restore the first pressure before the pressure variation.

3. The insertion apparatus according to claim 1, wherein the pressure detector is configured to detect a pressure variation value per predetermined time period in the subject or a time period during which the pressure in the subject changes.

4. The insertion apparatus according to claim 3, wherein
the pressure detector is configured to detect a time period during which the pressure variation in the subject continues based on the operation of the first air feeding pump or the first air suction pump, and when the pressure variation detected by the pressure detector continues for the predetermined time period or more, the controller detects the operation of the first air feeding pump or the first air suction pump.

5. The insertion apparatus according to claim 1, wherein
the first air feeding pump feeds a predetermined amount of gas into the subject via a first air feeding tube provided in the endoscope, the first air suction pump suctions the predetermined amount of gas from the inside of the subject to the outside of the subject via a first air suction tube provided in the endoscope, the second air feeding pump continuously feeds gas into the subject via a second air feeding tube, and the second air suction pump continuously suctions the gas containing particles from the inside of the subject to the outside of the subject via a second air suction tube.

6. The insertion apparatus according to claim 5, wherein the controller is configured to detect a switch operation of an air feeding switch provided in the first air feeding tube or a switch operation of an air suction switch provided in the first air suction tube to detect the operation on the first air feeding pump or the first air suction pump.

7. The insertion apparatus according to claim 5, wherein the second air feeding tube branches from the first air feeding tube and converges with the first air feeding tube at least in the insertion portion.

8. The insertion apparatus according to claim 5, wherein the second air suction tube branches from the first air suction tube and converges with the first air suction tube at least in the insertion portion.

9. The insertion apparatus according to claim 5, wherein at least one of the second air feeding tube and the second air suction tube is provided in an overtube that is inserted into the subject through the insertion portion.

10. The insertion apparatus according to claim 1, wherein the second air feeding pump and the second air suction pump are formed integrally, as a single pump including an air feeding mechanism and an air suction mechanism, the single pump being configured to filter the gas suctioned from the inside of the subject and feed the gas into the subject.

11. An insertion apparatus comprising:
an endoscope including an insertion portion to be inserted into a subject;
a first air feeding pump configured to feed gas into the subject based on a first user input operation;
a first air suction pump configured to suction gas from the inside of the subject to the outside of the subject based on a second user input operation;
a second air feeding pump configured to continuously feed gas into the subject independently of the first user input operation;
a second air suction pump configured to continuously suction gas from the inside of the subject to the outside of the subject independently of the second user input operation;
a pressure sensor configured to detect a pressure variation value per predetermined time period in the subject or a time period during which a pressure in the subject changes;
a controller configured to:
control an amount of gas fed into the subject by the second air feeding pump;
control an amount of gas suctioned to the outside of the subject by the second air suction pump,
perform a first control on the second air feeding pump and the second air suction pump to maintain the pressure in the subject at a first pressure by controlling the amount of gas fed from the second air feeding pump per predetermined time period to be equal to the amount of gas suctioned by the second air suction pump,
detect operation of the first air feeding pump or the first air suction pump, and
when the operation of the first air feeding pump or the first air suction pump is detected and the pressure detector detects that the pressure in the subject is changed from the first pressure to a second pressure which is different from the first pressure, and the second pressure continues for a predetermined time period or more, continue the first control to maintain the second pressure in the subject.

12. The insertion apparatus according to claim 11, wherein the second air suction pump is configured to continuously suction gas containing particles obstructing a view of the endoscope generated when a cauterization apparatus applies a high frequency current to the subject.

13. An operation method for an insertion apparatus comprising:
inserting an insertion portion of an endoscope into a subject of a living body;
inserting a cauterization apparatus jointly with the insertion portion into the subject;
detecting a pressure in the subject by a pressure detector; and
continuously feeding gas into the subject by a second air feeding pump independently of a first user input operation and continuously suctioning gas from the subject to the outside of the subject by a second air suction pump, independently of a second user input operation, the gas in the subject being generated when the cauterization apparatus applies a high frequency current to the living body, the gas in the subject being gas containing particles obstructing a view of the endoscope, wherein a controller performs first control on the second air feeding pump and the second air suction pump to maintain the pressure in the subject at a first pressure by controlling the amount of gas fed from the second air feeding pump per predetermined time period to be equal to the amount of gas suctioned by the second air suction pump, and when a user input operation of a first air feeding pump or a first air suction pump is detected and the pressure detector detects that the pressure in the subject is changed from the first pressure to a second pressure which is different from the first pressure, and the second pressure continues for a predetermined time period or more, continuing the first control to maintain the second pressure in the subject.

14. The operation method for the insertion apparatus according to claim 13, wherein when the pressure detector detects a pressure variation, the controller performs, independently of the detection of the operation of the first air feeding pump or the first air suction pump, a second control in which the amount of gas fed from the second air feeding pump is different from the amount of gas suctioned by the second air suction pump so as to restore the first pressure before the pressure variation.

* * * * *